(12) United States Patent
McClellan

(10) Patent No.: US 11,039,898 B2
(45) Date of Patent: Jun. 22, 2021

(54) MRI SAFE TISSUE EXPANDER PORT

(71) Applicant: William T. McClellan, Morgantown, WV (US)

(72) Inventor: William T. McClellan, Morgantown, WV (US)

( * ) Notice: Subject to any disclaimer, the term of this patent is extended or adjusted under 35 U.S.C. 154(b) by 150 days.

(21) Appl. No.: 16/173,079

(22) Filed: Oct. 29, 2018

(65) Prior Publication Data

US 2019/0239976 A1 Aug. 8, 2019

Related U.S. Application Data

(60) Provisional application No. 62/627,940, filed on Feb. 8, 2018.

(51) Int. Cl.
| | | |
|---|---|---|
| *A61F 2/12* | (2006.01) | |
| *A61B 90/00* | (2016.01) | |
| *A61M 39/02* | (2006.01) | |

(52) U.S. Cl.
CPC .............. *A61B 90/02* (2016.02); *A61B 90/39* (2016.02); *A61F 2/12* (2013.01); *A61M 39/0208* (2013.01); *A61B 2090/3954* (2016.02); *A61F 2250/0003* (2013.01); *A61M 2039/0238* (2013.01)

(58) Field of Classification Search
CPC ......................................................... A61F 2/12
USPC ......................................................... 623/7–8
See application file for complete search history.

(56) References Cited

U.S. PATENT DOCUMENTS

| 4,671,255 A | 6/1987 | Dubrul et al. |
| 4,800,901 A | 1/1989 | Rosenberg |
| 5,630,843 A | 5/1997 | Rosenberg |
| 5,879,297 A * | 3/1999 | Haynor .................... A61B 5/06 |
| | | 128/899 |

(Continued)

FOREIGN PATENT DOCUMENTS

| WO | 2011063349 A1 | 5/2011 |
| WO | 2011075731 A2 | 6/2011 |
| WO | 2018078446 A1 | 5/2018 |

OTHER PUBLICATIONS

Hawkin et al., "MRI Safety Information", Zimmer Biomet, http://www.zimmerbiomet.com/medical-professionals/support/mri.html, accessed Feb. 8, 2018; 3 pages.

(Continued)

*Primary Examiner* — Suzette J Gherbi
(74) *Attorney, Agent, or Firm* — Andrew D. Wright; Roberts Calderon Safran & Cole, P.C.

(57) ABSTRACT

Improvements for use with tissue expanders are provided. A tissue expander includes: a selectively inflatable and deflatable shell that is configured to be implanted; and an access port for selectively inflating and deflating the shell, the access port comprising a sidewall, a base at a first end, and a membrane at a second end opposite the first end, wherein the sidewall and the base of the access port are constructed of a material that is non-reactive with a magnetic resonance imaging (MRI) machine. In embodiments, the tissue expander includes a magnet at the access port. In embodiments, the magnet is configured with a physical size and magnetic force such that, when the tissue expander is implanted, the magnet is detectable by an external magnetometer sensor but is not detectable by an external dangle-magnet.

25 Claims, 4 Drawing Sheets

(56) References Cited

U.S. PATENT DOCUMENTS

| | | | |
|---|---|---|---|
| 5,882,353 A * | 3/1999 | VanBeek | A61B 90/02 623/8 |
| 5,944,023 A | 8/1999 | Johnson et al. | |
| 6,044,297 A | 3/2000 | Sheldon et al. | |
| 6,206,930 B1 | 3/2001 | Burg et al. | |
| 6,666,893 B2 | 12/2003 | Burg et al. | |
| 7,575,597 B2 | 8/2009 | Rehnke | |
| 7,736,391 B2 | 6/2010 | Schwibner et al. | |
| 7,871,438 B2 | 1/2011 | Corbitt | |
| 8,015,977 B2 | 9/2011 | Bertrand et al. | |
| 8,387,817 B1 | 3/2013 | Zelechonok | |
| 8,454,690 B2 | 6/2013 | McClellan | |
| 9,144,488 B2 | 9/2015 | Boyden et al. | |
| 9,268,915 B2 | 2/2016 | Holmes et al. | |
| 9,333,071 B2 | 5/2016 | Boyden et al. | |
| 9,814,566 B1 | 11/2017 | Cree | |
| 10,010,404 B2 | 7/2018 | McClellan | |
| 10,176,412 B2 | 1/2019 | Geissler et al. | |
| 10,252,145 B2 | 4/2019 | Tran et al. | |
| 10,588,737 B2 | 3/2020 | McClellan | |
| 2005/0061198 A1 | 3/2005 | Khan et al. | |
| 2007/0233273 A1 | 10/2007 | Connell | |
| 2007/0288095 A1 | 12/2007 | Wirtel et al. | |
| 2008/0033471 A1 | 2/2008 | Paz et al. | |
| 2008/0091175 A1 | 4/2008 | Frikart et al. | |
| 2008/0161929 A1 | 7/2008 | McCormack et al. | |
| 2009/0012372 A1 | 1/2009 | Burnett et al. | |
| 2009/0157180 A1 | 6/2009 | Schraga | |
| 2010/0256775 A1 | 10/2010 | Belhe et al. | |
| 2011/0153017 A1 | 6/2011 | McClellan | |
| 2011/0208311 A1 | 8/2011 | Janowski | |
| 2012/0041305 A1 | 2/2012 | Grissom et al. | |
| 2012/0165657 A1 * | 6/2012 | Groszmann | A61B 90/39 600/424 |
| 2012/0184893 A1 | 7/2012 | Thompson et al. | |
| 2012/0302874 A1 * | 11/2012 | Hollstien | A61B 5/4851 600/424 |
| 2013/0116664 A1 * | 5/2013 | Tai | A61M 39/0208 604/891.1 |
| 2013/0190796 A1 | 7/2013 | Tilson et al. | |
| 2013/0325120 A1 | 12/2013 | McClellan | |
| 2013/0338769 A1 | 12/2013 | Boyden et al. | |
| 2014/0121771 A1 | 5/2014 | Chitre et al. | |
| 2015/0327985 A1 * | 11/2015 | Hristov | A61B 8/481 623/8 |
| 2015/0327989 A1 * | 11/2015 | Boyden | A61B 5/686 623/8 |
| 2015/0374906 A1 * | 12/2015 | Forsell | A61F 5/0013 600/31 |
| 2016/0066979 A1 | 3/2016 | Mueller et al. | |
| 2016/0250017 A1 | 9/2016 | McClellan | |
| 2016/0310306 A1 | 10/2016 | Brister et al. | |
| 2017/0228627 A1 | 8/2017 | Geissler et al. | |
| 2017/0246019 A1 | 8/2017 | Miesse et al. | |
| 2018/0092736 A1 * | 4/2018 | Lee | A61B 17/06166 |
| 2018/0116823 A1 * | 5/2018 | Johannaber | A61B 5/4851 |
| 2019/0000656 A1 * | 1/2019 | Pool | A61F 5/003 |
| 2019/0015195 A1 * | 1/2019 | Chitre | A61F 2/12 |
| 2019/0025040 A1 * | 1/2019 | Andreason | A61B 34/20 |
| 2019/0111206 A1 * | 4/2019 | Forsell | A61M 5/14526 |
| 2019/0142574 A1 * | 5/2019 | Quiros | A61L 27/18 623/8 |
| 2019/0175334 A1 * | 6/2019 | Van Heugten | A61F 2/14 |
| 2019/0192044 A1 * | 6/2019 | Ravi | A61B 34/20 |
| 2019/0192326 A1 * | 6/2019 | Chen | A61F 2/12 |
| 2019/0282756 A1 * | 9/2019 | Hanson | A61M 5/1684 |
| 2019/0365277 A1 * | 12/2019 | Brister | A61B 5/062 |
| 2020/0078158 A1 * | 3/2020 | Popescu | A61F 2/08 |
| 2020/0129258 A1 * | 4/2020 | Feinberg | A61M 39/0208 |
| 2020/0129259 A1 | 4/2020 | Feinberg | |

OTHER PUBLICATIONS

International Search Report and Written Opinion issued in a corresponding application PCT/US19/17269 dated May 1, 2019, 8 pages.

Office Action in related U.S. Appl. No. 16/016,865 dated May 10, 2019, 7 pages.

International Search Report and Written Opinion issued in a application PCT/US2014/061075 dated Jan. 29, 2015, 7 pages.

* cited by examiner

MRI SAFE TISSUE EXPANDER PORT

This application claims priority to U.S. Provisional Application No. 62/627,940 filed Feb. 8, 2018, the contents of which are incorporated by reference herein in their entirety.

FIELD OF THE INVENTION

The invention generally relates to medical devices and associated methods of manufacture and use, and more particularly to tissue expanders.

BACKGROUND

Breast reconstruction with a tissue expander (TE) is currently the most common technique used for breast reconstruction. Typically immediately after the female has a mastectomy the reconstructive medical professional places a tissue expander which serves to stretch the skin and muscle in order to make room for a future implant or maintain the existing skin envelope. Prosthetic reconstruction of the breast, as a staged procedure with tissue expanders followed by implants, is a reliable method for breast reconstruction that offers favorable aesthetic and psychological results while adding only minimal additional surgical intervention. Today, the process usually involves the placement of a tissue expander under the pectoralis major muscle and remaining skin of the absent breast. The tissue expander is then gradually inflated over several weeks or months by periodic injections of saline, causing the stretching and expansion of the overlying skin and muscle coverage. When adequate coverage is achieved, the tissue expander is typically removed, and a permanent breast implant is placed into the expanded space.

Conventional tissue expanders include a shell and a port for selectively inflating and deflating the shell. The port includes a metal structure supporting a membrane that can be pierced by a needle to facilitate the inflating and deflating of the shell. Because the tissue expander is implanted under the patient's skin, the surgeon (or other medical professional) cannot visually see the port when attempting to access the port with a needle. Accordingly, a strong magnet may be included in the structure of the port, and the surgeon may use a dangle-magnet that is external to the patient to attempt to locate the port that is internal to the patient via the magnetic attraction between the dangle-magnet and the strong magnet included in the structure of the port. However, the strong magnet included in the structure of the port, and the metal structure of the port itself, can interact with an magnetic resonance imaging (MRI) and cause problems. For example, the MRI may cause heating of the strong magnet included in the structure of the port and this heating can lead to pain for the patient. The interaction between the MRI and the strong magnet can also cause movement of the strong magnet, and this can lead to dislodgement and/or rupture of the tissue expander with in the patient. Moreover, the interaction of the MRI and the metal structure of the port itself can cause unwanted artifacts in the output of the MRI. For these reasons, tissue expanders are contra-indicated for use with MRI's.

SUMMARY

In a first aspect of the invention, there is a tissue expander comprising: a selectively inflatable and deflatable shell that is configured to be implanted; and an access port for selectively inflating and deflating the shell, the access port comprising a sidewall, a base at a first end, and a membrane at a second end opposite the first end, wherein the sidewall and the base of the access port are constructed of a material that is non-reactive with a magnetic resonance imaging (MRI) machine. In embodiments, the tissue expander includes a magnet at the access port. In embodiments, the magnet is configured with a physical size and magnetic force such that, when the tissue expander is implanted, the magnet is detectable by an external magnetometer sensor but is not detectable by an external dangle-magnet. Aspects of the invention also include a method of manufacturing the tissue expander. Aspects of the invention also include a method of using the tissue expander.

In another aspect of the invention, there is a device configured to detect an implanted tissue expander, the device comprising: a housing comprising a display; and a magnetic sensor configured to detect a direction and a strength of a magnetic field of a magnet in the implanted tissue expander, wherein the device controls an output of the display based on signals received from the magnetic sensor. Aspects of the invention also include a method of manufacturing the device. Aspects of the invention also include a method of using the device to detect a tissue expander.

In another aspect of the invention, there is a system comprising: (i) a tissue expander comprising: a selectively inflatable and deflatable shell that is configured to be implanted; and an access port for selectively inflating and deflating the shell, the access port comprising a sidewall, a base at a first end, and a membrane at a second end opposite the first end, wherein the sidewall and the base of the access port are constructed of a material that is non-reactive with a magnetic resonance imaging (MRI) machine; and (ii) a device configured to detect the tissue expander when the tissue expander is implanted, the device comprising: a housing comprising a display; and a magnetic sensor configured to detect a direction and a strength of a magnetic field of a magnet in the implanted tissue expander, wherein the device controls an output of the display based on signals received from the magnetic sensor.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

According to aspects of the invention, a tissue expander includes a port that is constructed of non-metallic material(s). In embodiments, a magnet is attached to, or integrally formed with, the non-metallic material of the port. In particular embodiments, the magnet is structured and arranged to be detectable by an external magnetometer sensor, but to not be detectable by an external dangle-magnet. In this manner, the magnet may be made much smaller (both in physical size and magnetic force) compared to a magnet that designed for detection by an external dangle-magnet. By constructing the port from non-metallic material(s), and by making the magnet much smaller than normal, the inventive tissue expander port is safe for use with an MRI, in contrast to conventional tissue expanders that are contra-indicated for use with MRI's. In this manner, implementations of the invention provide improvements in tissue expander technology and application.

Figure 1:
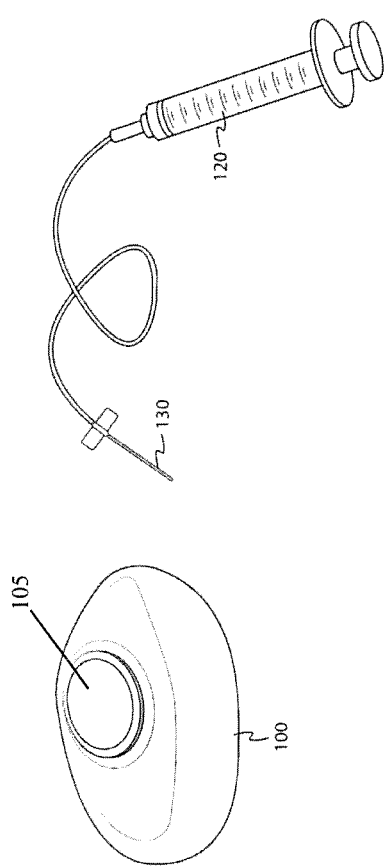
FIG. 1 shows a system used for tissue expansion, which may include a tissue expander and a fluid delivery system.

FIG. 1 shows a system used for tissue expansion, which may include a tissue expander 100 and a fluid delivery system 120. The tissue expander 100 includes an access port 105 (also called an implant port). The fluid delivery system 120 may include a needle 130 or other end used to access the interior of the tissue expander 100. The fluid delivery system 120 may provide a fluid to the interior (e.g., internal cavity defined by an implant shell 115) of the tissue expander 100 to cause the tissue expander 100 to expand. In some embodiments, the fluid delivery system 120 may also be used to access the interior of the tissue expander 100 to remove fluid from the tissue expander 100, which may cause the tissue expander 100 to contract or deflate.

Figure 2:
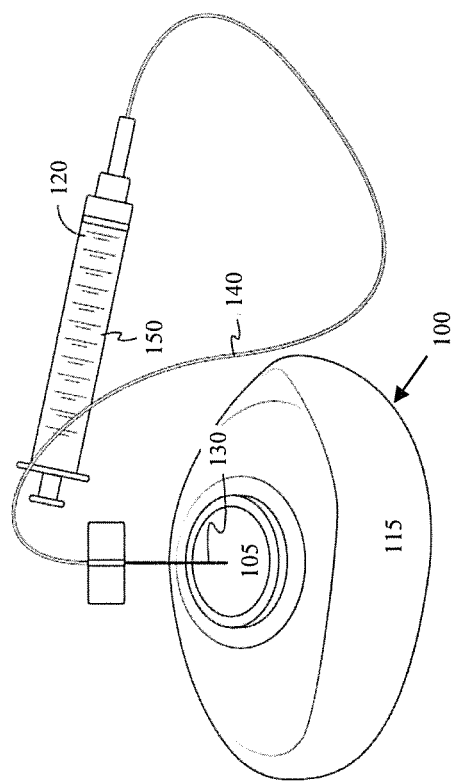
FIG. 2 shows an example of a fluid delivery system providing access to an access port of a tissue expander.

FIG. 2 shows an example of a fluid delivery system 120 providing access to an access port 105 of a tissue expander 100 comprising an implant shell 115. The fluid delivery system 120 may include a needle 130 and a tube 140 to provide fluid to the interior of the tissue expander 100 via the access port 105 (e.g., inflation/deflation port). The needle may puncture the access port 105 to provide fluid to, or remove fluid from, the interior (e.g., internal cavity) of the tissue expander. The access port 105 may be provided with a self-healing/sealing material that, after being punctured by a needle of the fluid delivery system 120, reforms an airtight and liquid tight seal. In some instances, the fluid delivery system 120 may utilize a tip other than a needle that may be capable of delivering a fluid to, and removing fluid from, the tissue expander 100.

A pressure differential may be created to cause fluid to flow into or out of the tissue expander 100. For example, a positive pressure may be provided from outside the tissue expander 100, which positive pressure causes inflation of the tissue expander 100. In one example, a syringe 150 may be used to provide the positive pressure. In another example, a negative pressure may be provided from within the tissue expander 100 to draw fluid out of the tissue expander 100 for deflation of the tissue expander 100. Alternatively, pumps or valves may be utilized to assist with fluid flow.

Figure 4:
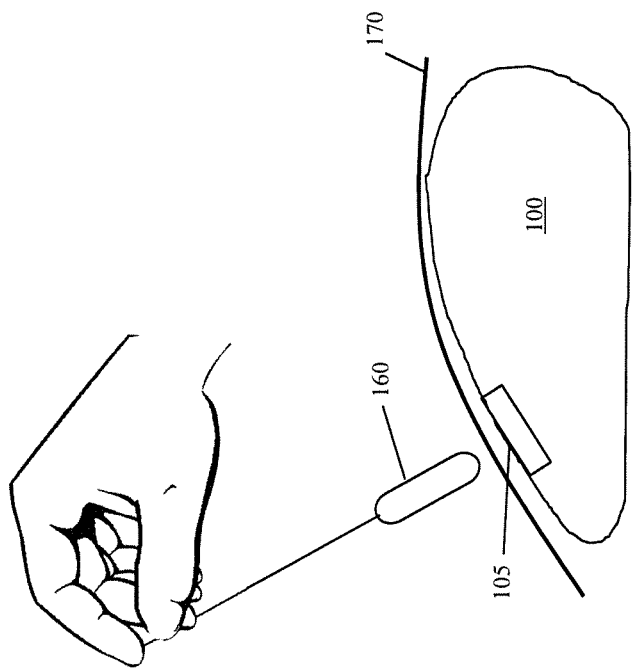
FIGS. 3 and 4 illustrate a method of locating a port of the tissue expander using a dangle-magnet.
Figure 3:
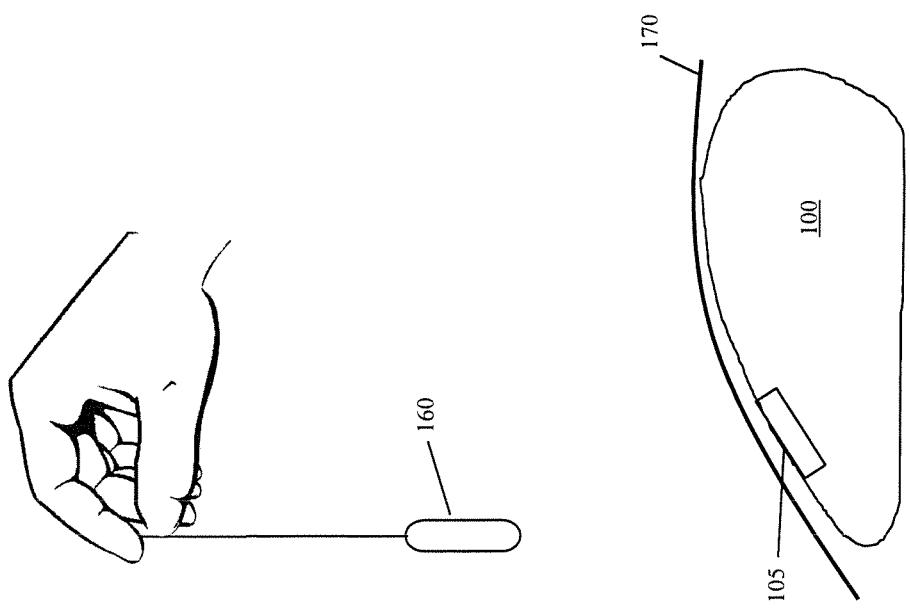

FIGS. 3 and 4 illustrate a method of locating the port 105 of the tissue expander 100 using a dangle-magnet 160. As shown in FIG. 3, the tissue expander 100 is implanted in a patient under the skin 170 of the patient. In this implanted state, a surgeon cannot visually see the port 105 because the port 105 is covered by the skin 170. Accordingly, the port 105 may be provided with a relatively strong magnet, and the surgeon may utilize an external dangle-magnet 160 to locate the port 105 via magnetic attraction between the strong magnet and the dangle-magnet 160. As depicted in FIGS. 3 and 4, the dangle-magnet 160 is drawn toward the port 105 when the dangle-magnet is moved within close proximity of the port 105, i.e., by the magnetic attraction force between the strong magnet and the dangle-magnet 160. In this manner, the surgeon may use the use the dangle-magnet 160 to locate the port 105. However, this method has drawbacks of being imprecise and requiring the use of a relatively large/strong magnet at the port 105.

Figure 5:
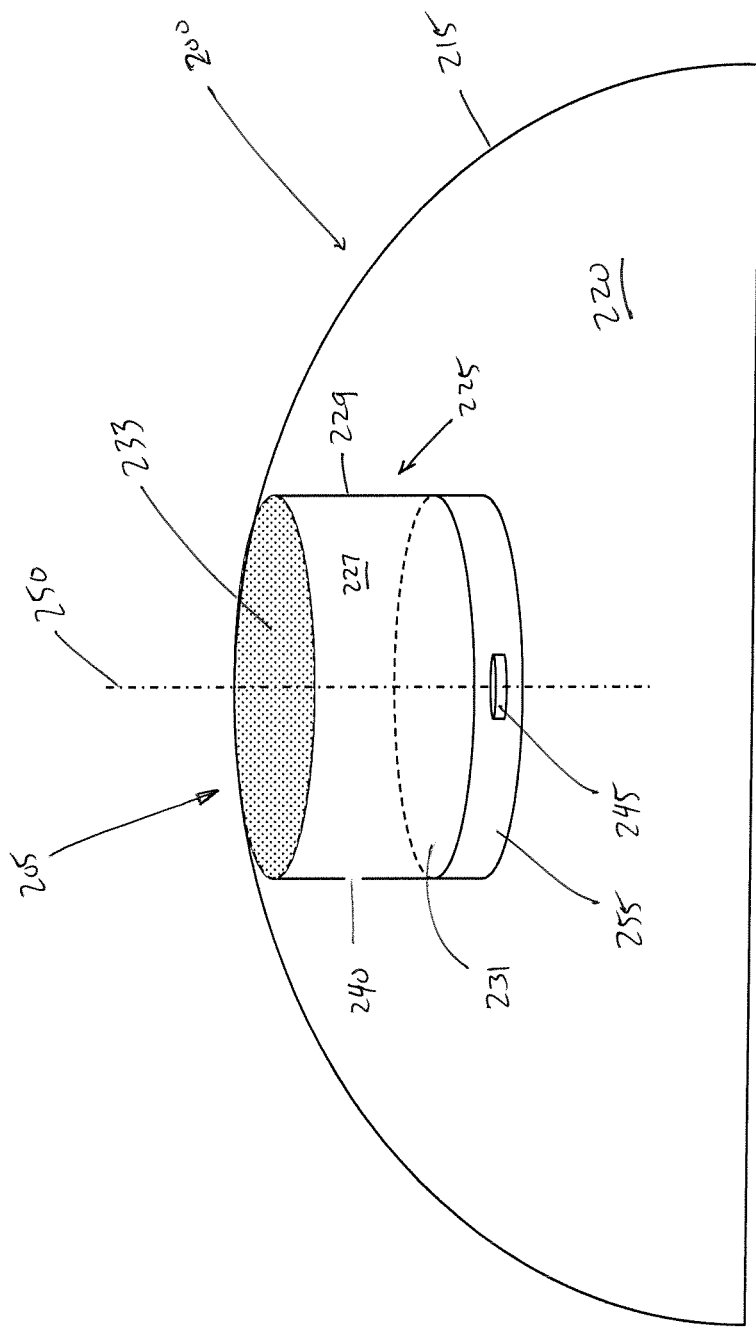
FIG. 5 shows a tissue expander including a access port in accordance with aspects of the invention.

FIG. 5 shows a tissue expander 200 including a access port 205 in accordance with aspects of the invention. In embodiments, the tissue expander 200 includes a shell 215 that defines an interior volume 220 that can be selectively inflated and deflated via the access port 205 in a conventional manner. In embodiments, the access port 205 includes a body 225 that defines an interior volume 227. For illustration, the body 225 is described herein in the shape of a cylinder; however, implementations of the invention are not limited to a cylinder, and instead the body 225 may have any suitable shape and configuration that are capable of performing the functions described herein. In embodiments, the body 225 includes a sidewall 229 and a base 231 at a first end. In embodiments, the access port 205 includes a membrane 233 at a second end of the body 225 opposite the first end. The membrane 233 may be a conventional or later-developed self-healing/sealing material that, after being punctured by a needle of a fluid delivery system (e.g., fluid delivery system 120), reforms an airtight and liquid tight seal. In this manner, the sidewall 229, the base 231, and the membrane 233 define the interior volume 227 of the body 225. The shell 215 may be the same as or similar to the shell 115, and the access port 205 may be configured to perform inflating and/or deflating functions similar to those described with respect to access port 105

In embodiments, the sidewall 229 includes at least one aperture 240 that provides fluid communication between the interior volume 227 of the access port 205 and the interior volume 220 of the shell 215. In this manner, a fluid delivery system (e.g., fluid delivery system 120 of FIGS. 1 and 2) may be used to selectively inflate and deflate the shell 215 in a conventional manner, e.g., by piercing the membrane with a needle 130 and creating a pressure differential with a syringe 150 to cause fluid to flow into or out of the tissue expander 200 via the at least one aperture 240.

According to aspects of the invention, the body 225 including the sidewall 229 and the base 231 is constructed of material that is non-reactive with an MRI. For example, the body 225 may be composed of one or more non-metallic and non-ferromagnetic materials such as one or more polymers. In embodiments, the material of the body 225 is sufficiently rigid to prevent puncture by a needle (e.g., needle 130) of a fluid delivery system (e.g., fluid delivery system 120). In this manner, when a needle of a fluid delivery system is pushed through the membrane 233, the sidewall 229 and the base 231 function as a hard-stop that limit the travel of the needle within the tissue expander 200. A specific example of a material that may be used for the body 225 is Delrin (e.g., polyoxymethylene); although implementations of the invention are not limited to this example, and other materials that are non-reactive with an MRI may be used. Although less preferable than non-metallic material, the body 225 may be composed of metallic material(s) that are non-ferromagnetic, including but not limited to: commercially pure titanium (CP Titanium), Ti-6Al-4V alloy, Ti-6Al-7Nb alloy, Co—Cr alloys (ASTM F75, F562, and F90), and tantalum.

With continued reference to FIG. 5, the port 205 according to aspects of the invention includes a magnet 245. In embodiments, the magnet 245 is much smaller (both in physical size and magnetic force) compared to a magnet used in port 105 designed for detection by an external dangle-magnet 160 as described with respect to FIGS. 3 and 4. In preferred embodiments, the magnet 245 is configured with a physical size and magnetic force that is detectable by an external magnetometer sensor, but to not be detectable by an external dangle-magnet. In this manner, the relatively smaller/weaker magnet 245 is safer for use in an MRI than the relatively larger/stronger magnet used in port 105 that is designed for detection by an external dangle-magnet 160.

The magnetic flux density (Gauss) and pull force are not directly related meaning that two magnets can have the same Gauss but different pull forces. They are related mainly based on the size and geometry of the magnet. For example, in similar locations relative to the center of the magnets, both a smaller magnet and a larger magnet can have the same Gauss reading but very different pull forces. A magnetometer measures the Gauss while the dangle-magnet is dependent on the pull force to find an implanted magnet. As a result, implementations of the invention use a magnet 245 that is smaller (i.e., less pull force where it cannot be found with another magnet) than a magnet used with a conventional dangle-magnet system, and find the smaller magnet 245 with a magnetometer instead of a dangle magnet. In this manner, implementations of the invention can employ a smaller implanted magnet 245 with a lower pull force (compared to a magnet used with a dangle-magnet system) and find it with the magnetometer. This smaller implanted magnet 245 with a lower pull force makes implementations of the invention MRI-safe, whereas a conventional implanted magnet that is sufficiently strong to be found with an external dangle-magnet is not MRI safe.

For example, a conventional magnet used in a port of a conventional tissue expander has a diameter of 1.015 inches and a thickness of 0.095 inches. This conventional magnet is sized in this manner to de detectable by a dangle-magnet when the tissue expander is implanted in a patient, e.g., as shown in FIGS. 3 and 4. In contrast to this conventional magnet, the magnet 245 used in embodiments of the invention can have a diameter of between 1 mm and 7 mm and can be found when implanted in a patient using a magnetometer device (such as device 300 described herein). In this manner, the magnet 245 is configured with a physical size and magnetic force such that, when the tissue expander is implanted, the magnet 245 is detectable by an external magnetometer sensor but is not detectable by an external dangle-magnet.

In an exemplary implementation of the invention, Polymer Port prototypes utilizing 4 mm diameter×2 mm height Zinc coated neodymium magnets 245 were evaluated and tested against conventional port designs using the Shellock MRI test method, which is the acceptable method used by ASTM. The Polymer Port technology with magnet 245 can be located using the device 300 described herein, but are otherwise undetectable by standard methods including a dangle-magnet. In this manner, the magnet 245 is configured with a physical size and magnetic force such that, when the tissue expander is implanted, the magnet 245 is detectable by an external magnetometer sensor but is not detectable by an external dangle-magnet. In experiments, a 1.5—Tesla Magnetom was used for deflection angle and pull force evaluation. The Polymer Port technology resulted in a ~98.8% reduction in pull force compared to that of a standard magnetic port. Artifact evaluation was also conducted to compare the Polymer Port technology with conventional port designs. The cross-sectional area of the artifact was reduced by ~80.5% when compared to conventional port designs. In some implementations, the pull force of the Polymer Port technology using magnet 245, when placed in an MRI, is less than the gravity acting on the overall tissue expander and imaging artifact will be minimal.

In embodiments, the magnet 245 is embedded in a structure 255 below the base 231 of the body 225. The structure 255 may be part of the body 225 (e.g., integrally molded with the sidewall 229 and the base 231), or alternatively may be connected to the body 225 (e.g., adhered or fused to the base 231). The structure 255 may be composed of the same material as the body 225, or may be composed of a different material that is still non-reactive with an MRI. In embodiments, the magnet 245 is centered in the port 205 to facilitate aiming the needle to the membrane 233 for selectively inflating and deflating the tissue expander 200. For example, the magnet 245 and the body 225 may be coaxial along axis 250 as depicted in FIG. 5.

Figure 7:
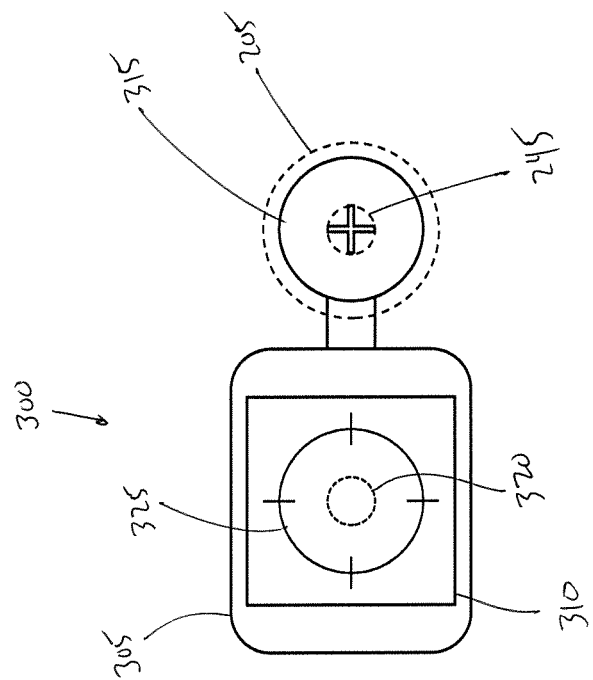
FIGS. 6 and 7 show a device configured to detect a magnet of a port in accordance with aspects of the invention.
Figure 6:
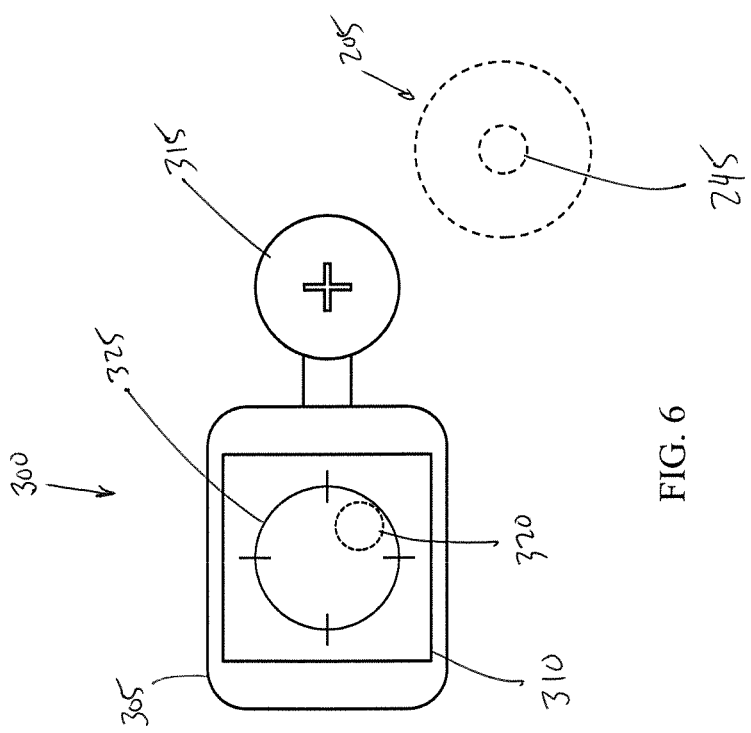

FIGS. 6 and 7 show a device 300 configured to detect the magnet 245 of the port 205 in accordance with aspects of the invention. In embodiments, the device 300 comprises a portable or a hand held computing device is provided with hardware and software that is structured and arranged to locate the magnet 245 of a port 205 of a tissue expander 200 that is under the skin of a patient (i.e., implanted under the skin, not visible to the naked eye), and display a location of the port on a visual display of the computing device. The device 300 may comprise a housing 305, a display 310, and a sensor 315. The housing 305 may house computer components including but not limited to a computer memory, a computer processor, and a power supply. The memory may store program code that is executed by the processor to perform one or more of the functions described herein, including but not limited to controlling the output of the display 310 based on signals received from the sensor 315. The display 310 may be any desired type of visual display including but not limited to, LCD, LED, etc.

In embodiments, the sensor 315 is configured to detect a direction and a strength of a magnetic field of the magnet 245, and may comprise a magnetometer for example. Based on signals from the sensor 315, the computer processor controls the display 310 to show a graphic that depicts an indication 320 of the magnet 245 relative to the frame of reference 325 (which may be a crosshair or other frame of reference). As depicted in FIGS. 6 and 7, when the device 300 is moved relative to the access port 205, the display 310 changes the location of the indication 320 relative to the frame of reference 325. In this manner, when the tissue expander 200 is implanted under the skin of a patient, the surgeon may move the device 300 over the skin of the patient and determine a location of the access port 205 using the display 310.

In embodiments, the device 300 may be optimized based on the magnet 245. For example, the device 300 may be manufactured and programmed based on a predefined nominal magnitude of a magnetic force of the magnet 245. In this manner, the magnet 245 may be made very small (to minimize interaction with an MRI), and the device 300 may be tuned to precisely detect the relatively small force of the magnet 245. The device 300 may also include a spacer below the sensor 315, such that the spacer is between the sensor 315 and the skin, and the device 300 may be optimized to detect the magnet 245 based on the dimensional extent of this spacer. In embodiments, the sensor 315 comprises plural magnetometers, the respective signals of which the computer processor uses together to determine a position of the magnet 245, e.g., via trilateration and/or triangulation. In this manner, the device 300 may be optimized to detect very small magnets, e.g., 1 mm diameter and less.

The access port 205 and magnet 245 as described herein may be incorporated into conventional tissue expanders, such as those described in: U.S. Pat. No. 4,800,901; U.S. Patent Publication No. 2007/0233273; U.S. Pat. Nos. 6,666,893; 6,206,930; 7,575,597; 8,454,690, and U.S. Patent Publication No. 2016/0250017, the disclosures of all of which are incorporated by reference herein in their entirety. A tissue expander in accordance with aspects of the invention may include the access port 205 and magnet 245 as described herein in combination with features, components, or characteristics of other implants such as those described in the aforementioned patents and patent publications.

Additional aspects of the invention include manufacturing a tissue expander with the access port 205 and magnet 245 as described herein. Additional aspects of the invention include a system comprising the port 205 and magnet 245 as described herein, separate from a tissue expander, and associated methods of manufacturing the port 205 and magnet 245 separate from a tissue expander. Further aspects of the invention include manufacturing and/or using the device 300 as described herein. Even further aspects of the invention include providing instructions for using the device 300 and a tissue expander having access port 205 and magnet 245 described herein. The instructions may be at least one of printed and video.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A tissue expander, comprising:
a selectively inflatable and deflatable shell that is configured to be implanted;
an access port for selectively inflating and deflating the shell, the access port comprising a sidewall, a base at a first end, and a membrane at a second end opposite the first end; and
a magnet at the access port,
wherein the sidewall and the base of the access port are constructed of a material that is non-reactive with a magnetic resonance imaging (MRI) machine.

2. The tissue expander of claim 1, wherein the material is a non-metallic and non-ferromagnetic material.

3. The tissue expander of claim 1, wherein the material is a non-metallic and non-ferromagnetic polymer.

4. The tissue expander of claim 1, wherein the material is polyoxymethylene.

5. The tissue expander of claim 1, wherein:
the membrane is pierceable by a needle; and
the sidewall and the base function as a hard-stop that limit travel of the needle within access port after the needle has pierced the membrane.

6. The tissue expander of claim 1, wherein the magnet has a diameter less than half a diameter of the base.

7. The tissue expander of claim 6, wherein the magnet is embedded in the material.

8. The tissue expander of claim 7, wherein the magnet is under the base.

9. The tissue expander of claim 7, wherein the magnet is centered in the access port.

10. The tissue expander of claim 1, wherein the magnet is sized and shaped such that there is no significant heating, dislodgment, or artifact produced when the magnet is influenced by the MRI.

11. The tissue expander of claim 1, wherein the magnet is configured with a physical size and magnetic force such that, when the tissue expander is implanted, the magnet is detectable by an external magnetometer sensor but is not detectable by an external dangle-magnet.

12. A device configured to detect an implanted tissue expander, the device comprising:
a housing comprising a display; and
a magnetic sensor configured to detect a direction and a strength of a magnetic field of a magnet in the implanted tissue expander,
wherein the device controls an output of the display based on signals received from the magnetic sensor, and
the magnet is located at an access port of the of the tissue expander for selectively inflating and deflating a shell of the tissue expander.

13. The device of claim 12, wherein the output of the display comprises a graphic that depicts an indication of a location of the magnet relative to a frame of reference.

14. The device of claim 12, further comprising a computer memory, a computer processor, and a power supply in the housing, wherein the computer memory stores program code that is executed by the computer processor to perform the controlling the output of the display based on signals received from the magnetic sensor.

15. A method comprising using the device of claim 12 to detect a tissue expander that is implanted under the skin of a patient.

16. A system, comprising:
(i) a tissue expander comprising: a selectively inflatable and deflatable shell that is configured to be implanted; and an access port for selectively inflating and deflating the shell, the access port comprising a sidewall, a base at a first end, and a membrane at a second end opposite the first end, wherein the sidewall and the base of the access port are constructed of a material that is non-reactive with a magnetic resonance imaging (MRI) machine; and
(ii) a device configured to detect the tissue expander when the tissue expander is implanted, the device comprising: a housing comprising a display; and a magnetic sensor configured to detect a direction and a strength of a magnetic field of a magnet in the implanted tissue expander, wherein the device controls an output of the display based on signals received from the magnetic sensor,
wherein the magnet is located at the access port, and the magnet is centered in the access port.

17. The system of claim 16, wherein the material is a non-metallic and non-ferromagnetic material.

18. The system of claim 17, wherein the material is polyoxymethylene.

19. The system of claim 16, wherein:
the membrane is pierceable by a needle; and
the sidewall and the base function as a hard-stop that limit travel of the needle within access port after the needle has pierced the membrane.

20. A system, comprising:
(i) a tissue expander comprising: a selectively inflatable and deflatable shell that is configured to be implanted; and an access port for selectively inflating and deflating the shell, the access port comprising a sidewall, a base at a first end, and a membrane at a second end opposite the first end, wherein the sidewall and the base of the access port are constructed of a material that is non-reactive with a magnetic resonance imaging (MRI) machine; and
(ii) a device configured to detect the tissue expander when the tissue expander is implanted, the device comprising: a housing comprising a display; and a magnetic sensor configured to detect a direction and a strength of a magnetic field of a magnet in the implanted tissue expander, wherein the device controls an output of the display based on signals received from the magnetic sensor,
wherein the magnet is located at the access port, and
wherein the magnet has a diameter less than half a diameter of the base.

21. The system of claim 16, wherein the magnet is embedded in the material.

22. The system of claim 16, wherein the magnet is under the base.

23. The system of claim 16, wherein the magnet is configured with a physical size and magnetic force such that, when the tissue expander is implanted, the magnet is detectable by the magnetic sensor of the device, but is not detectable by an external dangle-magnet.

24. The system of claim 16, wherein the output of the display comprises a graphic that depicts an indication of a location of the magnet relative to a frame of reference.

25. The system of claim 16, further comprising a computer memory, a computer processor, and a power supply in the housing, wherein the computer memory stores program code that is executed by the computer processor to perform the controlling the output of the display based on signals received from the magnetic sensor.

* * * * *